(12) United States Patent (10) Patent No.: US 12,636,413 B2
Boddie (45) Date of Patent: May 26, 2026

(54) BREAST PUMP SOUND SUPPRESSOR

(71) Applicant: Restful Pump, Inc., Pembroke, MA (US)

(72) Inventor: Micolene Boddie, Marshfield, MA (US)

(73) Assignee: RESTFUL PUMP, INC., Pembroke, MA (US)

( * ) Notice: Subject to any disclaimer, the term of this patent is extended or adjusted under 35 U.S.C. 154(b) by 1092 days.

(21) Appl. No.: 17/710,118

(22) Filed: Mar. 31, 2022

(65) Prior Publication Data

US 2023/0310721 A1 Oct. 5, 2023

(51) Int. Cl.
*A61M 1/06* (2006.01)
*A61M 1/00* (2006.01)

(52) U.S. Cl.
CPC .............. *A61M 1/062* (2014.02); *A61M 1/80* (2021.05)

(58) Field of Classification Search
CPC ...... A61M 1/06–0697; A61M 5/14244; A61M 2005/14272; A61M 2005/14268
See application file for complete search history.

(56) References Cited

U.S. PATENT DOCUMENTS

| 7,311,062 B2 | 12/2007 | Bilgery |
| 7,806,855 B2 | 10/2010 | Kliegman |
| 7,833,190 B1 | 11/2010 | Hall |

| 8,052,635 B1 | 11/2011 | Kelly | |
| 9,278,167 B2 | 3/2016 | Aalders | |
| 2001/0050222 A1* | 12/2001 | Choi ................... G02F 1/13439 204/192.15 |
| 2008/0090445 A1* | 4/2008 | Luzbetak ................ A61M 1/84 439/346 |
| 2011/0270162 A1 | 11/2011 | Guo | |
| 2015/0265753 A1* | 9/2015 | Prentice .................. A61M 1/74 604/74 |
| 2016/0067393 A1* | 3/2016 | Barnes .................... A61M 1/06 604/74 |
| 2018/0110906 A1* | 4/2018 | Barack .............. A61M 1/06935 |
| 2019/0083688 A1 | 3/2019 | Sutton | |

FOREIGN PATENT DOCUMENTS

| CN | 203577018 U | 5/2014 |
| CN | 204170165 U | 2/2015 |
| TW | 201617101 A | * 5/2016 |

OTHER PUBLICATIONS

Chang English Translation (Year: 2016).*

* cited by examiner

*Primary Examiner* — Courtney B Fredrickson

(74) *Attorney, Agent, or Firm* — Troutman Pepper Locke LLP

(57) ABSTRACT

A sound suppressor for a breast pump. The sound suppressor for the breast pump is operable to reduce noise coming from the breast pump when in operation. Breast pumps are known in the art to produce a distinctive and fairly loud noise, causing breast pumping mothers to feel agitated. The sound suppressor of the present disclosure operates to reduce and in some cases nearly eliminate sound coming from the breast pump.

20 Claims, 7 Drawing Sheets

BREAST PUMP SOUND SUPPRESSOR

BACKGROUND

Technical Field

The present disclosure relates generally to breast pumping systems. More particularly the present disclosure relates to a sound-insulating cover that can cover a breast pump, making it substantially quieter.

Description of Related Art

Feeding infant children using breastmilk has a number of advantages from both a health, financial, and convenience perspective. In many instances, to build up a store of milk for feeding the infant, mothers will pump milk for later consumption. Breast pumping is performed by many working mothers so that breast milk can be used to feed an infant child even when the mother is separate from the child. For example, working mothers who send their children to daycare, or mothers who wish other caretakers to feed the child find pumping breast milk to be a necessity.

Breast pumps are common machines made by a number of different manufacturers. In many instances, these machines make a repetitive loud noise when in operation. This noise is distracting and can lead to disruption in pumping and agitation of the pumping mother. Further, many women pump in public or semi-public settings such as in an office or cubicle. The telltale noise of the breast pump often makes women feel uncomfortable and self-conscious.

Moreover, as is well known by all parents of babies, a sleeping baby can be easily awakened, and the parenting break provided by a sleeping baby is precious time. In many cases, the nursing mother can use the nap times for a baby to pump breast milk. However, if the noise from the pump wakes the baby, not only is the precious time for the parent wasted, but the pumping is interrupted. Interrupted pumping leads to less milk collection, as well wasted milk leaking from the "let down" of milk, and disrupted milk production, as milk supply is largely dictated by demand created from the pumping. Therefore, the sound of a pump causing a sleeping baby to wake can be extremely problematic.

Therefore, what is needed is breast pumping "silencer" or muffler which can cover the breast pump and limit the sound it gives off.

SUMMARY

The subject matter of this application may involve, in some cases, interrelated products, alternative solutions to a particular problem, and/or a plurality of different uses of a single system or article.

In one aspect, a sound suppressor for a breast pump is provided. The sound suppressor is formed of a body which includes a sound-insulating material. The body defines an interior space into which a breast pump may fit and be contained and an opening allowing access to the interior. The body of the sound suppressor also has a transparent or translucent material forming a window. This window allows operation of buttons of a control system of the pump and also allows viewing a display through the window. The sound suppressor for the breast pump further has at least one pass-through extending through the body to allow a passage of at least one of a tube or power cord of the breast pump. As such, a power cord and/or a tube for drawing pressure by the breast pump can pass through the sound suppressor and allow operation of the device without allowing escape of excess sound.

In another aspect, a breast pumping assembly is provided. The breast pumping assembly includes a breast pump held within a sound suppressor for a breast pump. The sound suppressor for the breast pump is formed of a body which includes a sound-insulating material. The body defines an interior space into which the breast pump is positioned. The breast pump is contained and an opening allowing access to the interior. The body of the sound suppressor also has a transparent or translucent material forming a window. This window allows operation of buttons of a control system of the pump and also allows viewing a display through the window. The sound suppressor for the breast pump further has at least one pass-through extending through the body to allow a passage of at least one of a tube or power cord of the breast pump. A power cord and/or a tube for drawing pressure by the breast pump pass through the sound suppressor and allow operation of the device without allowing escape of excess sound.

In yet another aspect, a method of suppressing sound from a breast pump is provided. The method involves placing a breast pump into an interior space of a sound suppressor for a breast pump and closing the suppressor. Next, a tube is connected to the breast pump through the body of the sound suppressor. Further, a power cord is connected to the breast pump through the body of the sound suppressor. The breast pump is then activated through a window of the body of the sound suppressor.

DETAILED DESCRIPTION

Figure 1:
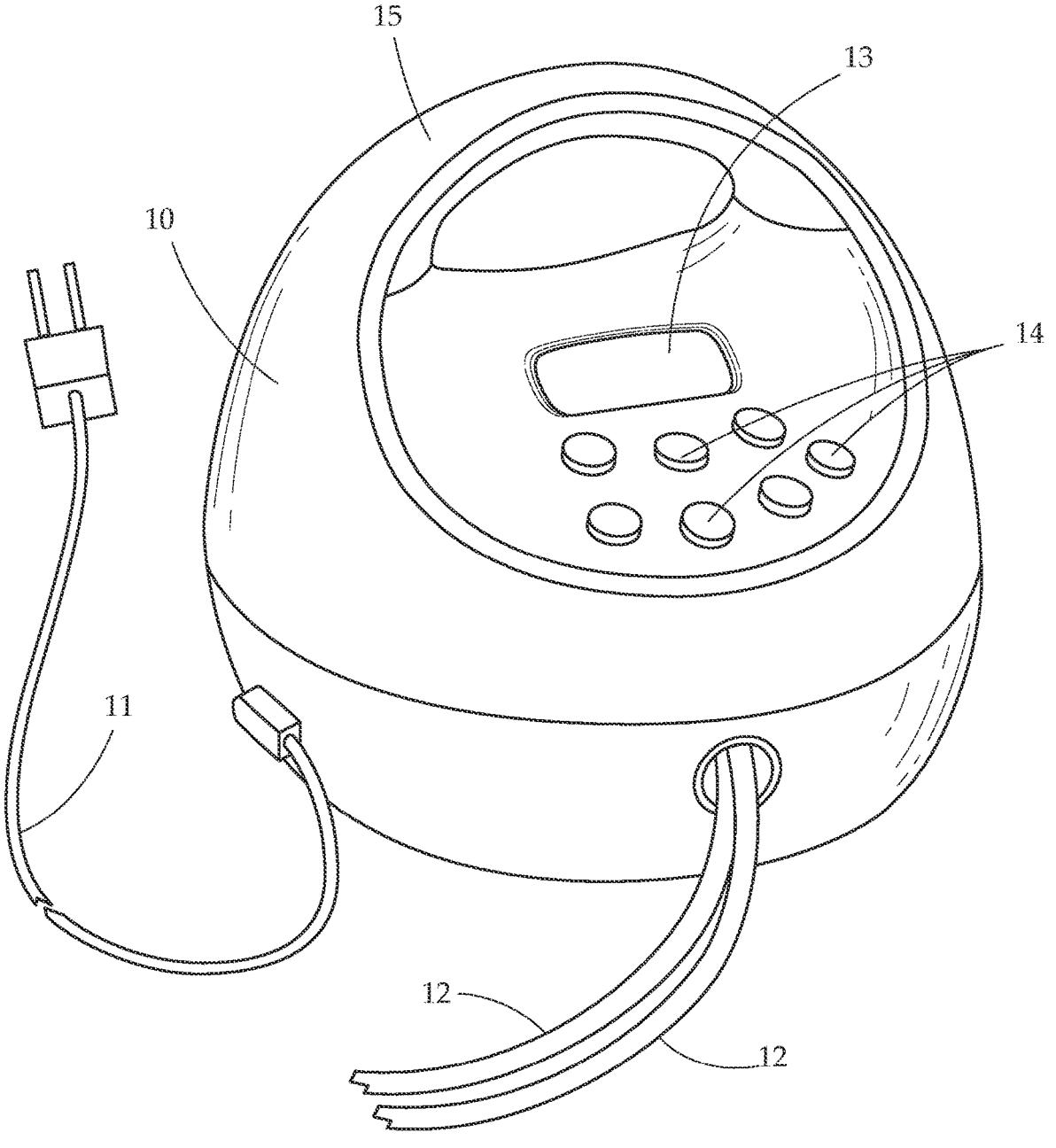
FIG. 1 provides a view of a breast pump known in the art.

The detailed description set forth below in connection with the appended drawings is intended as a description of presently preferred embodiments of the invention and does not represent the only forms in which the present disclosure may be constructed and/or utilized. The description sets forth the functions and the sequence of steps for constructing and operating the invention in connection with the illustrated embodiments.

Generally, the present disclosure concerns a sound-insulating cover for a breast pump. Referred to herein as a sound suppressor. It is well known that breast pumps make a loud, distinctive rhythmic noise during the pumping and release operations of the breast pump. Not only is this sound noisy, but it is distinctive such that anyone within earshot can tell that a woman is pumping breast milk. Pumping is a generally private and intimate activity and many women can feel exposed, vulnerable, and self-conscious during the pumping. Moreover, the loud noise can be irritating and distracting, preventing a pumping woman from relaxing and resting during the process. Therefore, the loud and distinctive noise of the breast pump essentially announces to anyone within ear shot that a woman is pumping, leading to a less relaxing experience during pumping. Feeling restful and relaxed is very important during pumping because it leads to substantially improved milk expression.

Accordingly, the present disclosure relates to a sound suppressor for a breast pump. This sound suppressor is formed of a body which is sound-insulating and which is sized and configured to cover and optionally enclose the breast pump. The body is formed of a sound insulating material such as a heavy fabric, plastic material, or the like, fabric layers enclosing a batting material, a sound insulating foam, a weighted material to prevent transfer of sound vibrations, and the like, as well as combinations thereof. The body defines an opening and interior space such that the breast pump can fit within the interior via passing through the opening. In some embodiments the opening may be closed to prevent sound from escaping. In other embodiments, the opening may sit flush or approximately flush against the surface on which the breast pump is sitting, thereby effectively closing the opening via the surface holding the breast pump and sound suppressor. An access window may be formed in the body of the sound suppressor. The access window may both allow viewing of a display on the breast pump, if present, as well as allow operation of the breast pump by allowing a pushing or actuation of buttons on the breast pump. At the same time, the window is sealed to prevent escape of sound vibrations. In some embodiments, the body defines a pass through to allow passage of a cord and/or tube of the breast pump.

The body of the sound suppressor comprises a sound-insulating material which is a material that meaningfully suppresses the sound coming from the breast pump. This material may be any material capable of limiting the sound coming from the breast pump including, but not limited to: A heavy fabric, membrane, or other flexible material which absorbs sound vibrations, a batting material, a foam, a weighted layer within the material, and the like.

The window defined in the body material is, in many embodiments, a transparent or translucent flexible plastic layer which allows viewing of a display on the breast pump, and also, by way of its flexibility, allows a user to push buttons on the pump through the window. In one embodiment, the window may be formed of two layers of a transparent or translucent flexible plastic material. These two layers may be spaced apart at their perimeter by, for example, a spacer, including but not limited to a sound absorbing foam spacer. This spacing apart of the two layers at least at their perimeter creates an air space between the two which provides for additional sound insulation. Of course, other structures and materials may be used without straying from the scope of this invention.

The opening of the body of the sound suppressor may have a closure to allow closing of the opening, thereby limiting sound escape through the opening. The closure may be any structure capable of covering the opening or reducing its size. Closures may include, but are not limited to a cover flap, a cinch cord and cord lock, hook and loop fasteners such as Vlecro®, buttons, snaps, magnetic closure, toggles, adhesive, a folding or rolling with snap closure, combinations of any of these, and the like. In other embodiments, a closure may not be needed, and an open bottom of the body may sit flat on a surface, thereby enclosing the pump and limiting escape of the sound. In further embodiments, the body may be custom made to fit a particular type of breast pump. For example, the sound suppressor may be specifically sized and configured to fit a Spectra® pump in one embodiment, and sized and configured to fit a Medela® pump. In another embodiment, a one-size-fits-all or one-size-fits-most sound suppressor may be used to allow for a single design to be used on many different breast pumps.

In certain cases, breast pumps may be wearable or portable and need not sit on a desktop or other flat surface. In such embodiments, the sound suppressor may be designed to enclose the portable pump. The opening of the body may be on a top, side, bottom, or the like for enclosing the portable pumps. In many cases, the sound suppressors for portable pumps may have the closure or closures to ensure that the body surrounds the pump and limits escape of sound. In a particular embodiment, a pump may be directly attached to a single bottle and single breast pumping flange. In such an embodiment, the sound suppressor may cover at least the pump, and in some cases may cover the pump as well as all or a portion of the bottle and/or flange to limit escape of sound from the pump. In this embodiment, when the breast pumping mother is pumping both breasts at a time, one sound suppressor for each breast pump may be used.

The body may have one or more pass through openings which allows things such as a power cord and pump tubes to pass through the sound suppressor and connect to the breast pump. Typically, breast pumps have a power cord and two suction tubes, one for each breast. Accordingly, in varying embodiments, the sound suppressor may have two pass throughs (one for a power cord and one for the two suction tubes) or may have three pass throughs (one for the power cord and two fore the two suction tubes). Of course, various configurations may be used without straying from the scope of this invention. In a particular embodiment, each pass through may comprise a gasket which flexes to allow passage of an item but provides an element of a seal around the item passing through, further closing the opening and limiting sound escape.

In one embodiment, an air inlet or other passage allowing air flow between the breast pump and outside atmosphere. This may help to prevent an overheating of the breast pump, and access for air to flow to the pump to ensure proper pump function. A flap, valve, or gasket may be positioned around the air flow passage to limit or prevent escape of sound by disrupting a clear flow path of air through the air flow passage.

FIG. 1 provides a view of a prior art breast pump known in the art. The breast pump 10 has a top handle 15 for easy carrying. A display 13 shows device status such as pumping intensity, speed, time, and other settings and status indications. A series of buttons 14 allows a user to turn the pump on and off, control setting such as strength and speed, set timers and the like. Two suction tubes 12 extend from the pump 10 and connect to a port on the pump 10. A power cord 11 connects to a wall outlet and provides electrical power for the breast pump 10.

Figure 2:
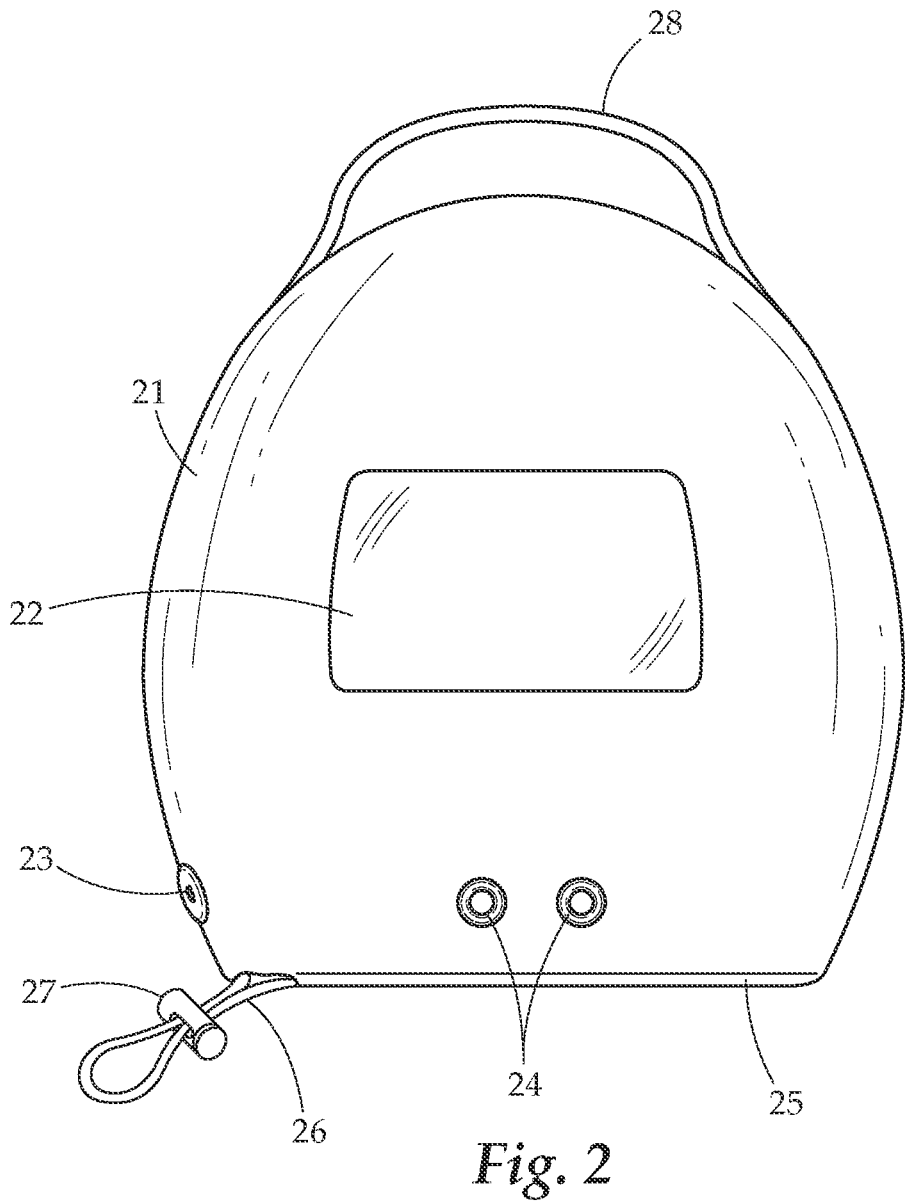
FIG. 2 provides an elevation view of an embodiment of the present disclosure.

FIG. 2 shows a view of an embodiment of the sound suppressor for the breast pump. The sound suppressor has a body 21 which defines the suppressor structure. A handle 28 allows a user to remove the sound suppressor from the breast pump and in some cases allows the user to carry both the sound suppressor and breast pump. As noted, the body 21 comprises a sound-insulating material and is able to greatly reduce noise from the breast pump. In the view shown, the body 21 comprises two layers of material, an inner and outer, and then an interior batting layer sandwiched between the inner and outer layers. Of course, other configurations are well within the scope of this invention such as foam sound insulation, heavy fabric sound insulation, a weighted layer (such as a thick fabric, membrane, or the like configured to be heavier than other layers of the body, in addition to other layers, and the like.

The body 21 further defines an access window 22 formed, in this embodiment, of a flexible transparent or translucent plastic. This allows viewing of the display 13 and control buttons 14 of the breast pump. Two pass through openings 24 allow passage of the breast pump suction tubes 12. These pass throughs 24 are formed as openings through the body to access the interior space where the breast pump is to be located. In this embodiment, the pass throughs 24 have a gasket with x shaped openings such that when the tube passes through, the portions of the gasket can flex but at least partially seal against the tube, limiting escape of the sound. Similarly, pass through 23 allows passage of the electrical cord 11. In this embodiment, the pass through 23 has a gasket with an x shaped opening such that when the cord passes through, the portions of the gasket can flex but at least partially seal against the cord, limiting escape of the sound. A closure is positioned at the bottom of the body 21 around the opening (not shown in this FIG.). The closure, in this embodiment, is a cinch cord 26 and cord lock 27. The body 21 can be placed over the breast pump 10 and then the cinch cord 26 drawn tight and locked in place with the cord lock 27, closing the opening and limiting noise escape.

Figure 3:
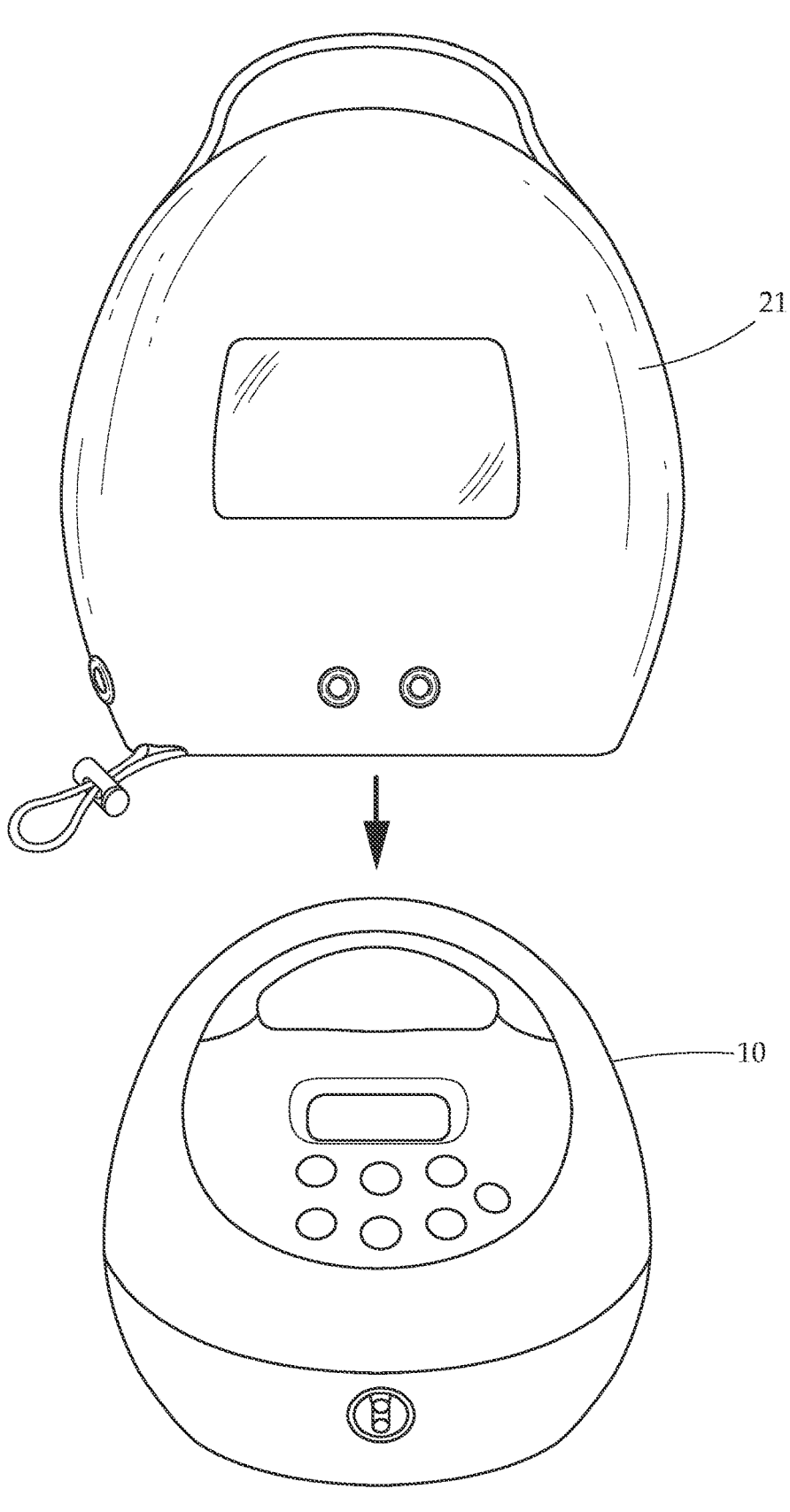
FIG. 3 provides a view of an embodiment of the present disclosure being applied to cover a breast pump.
Figure 4:
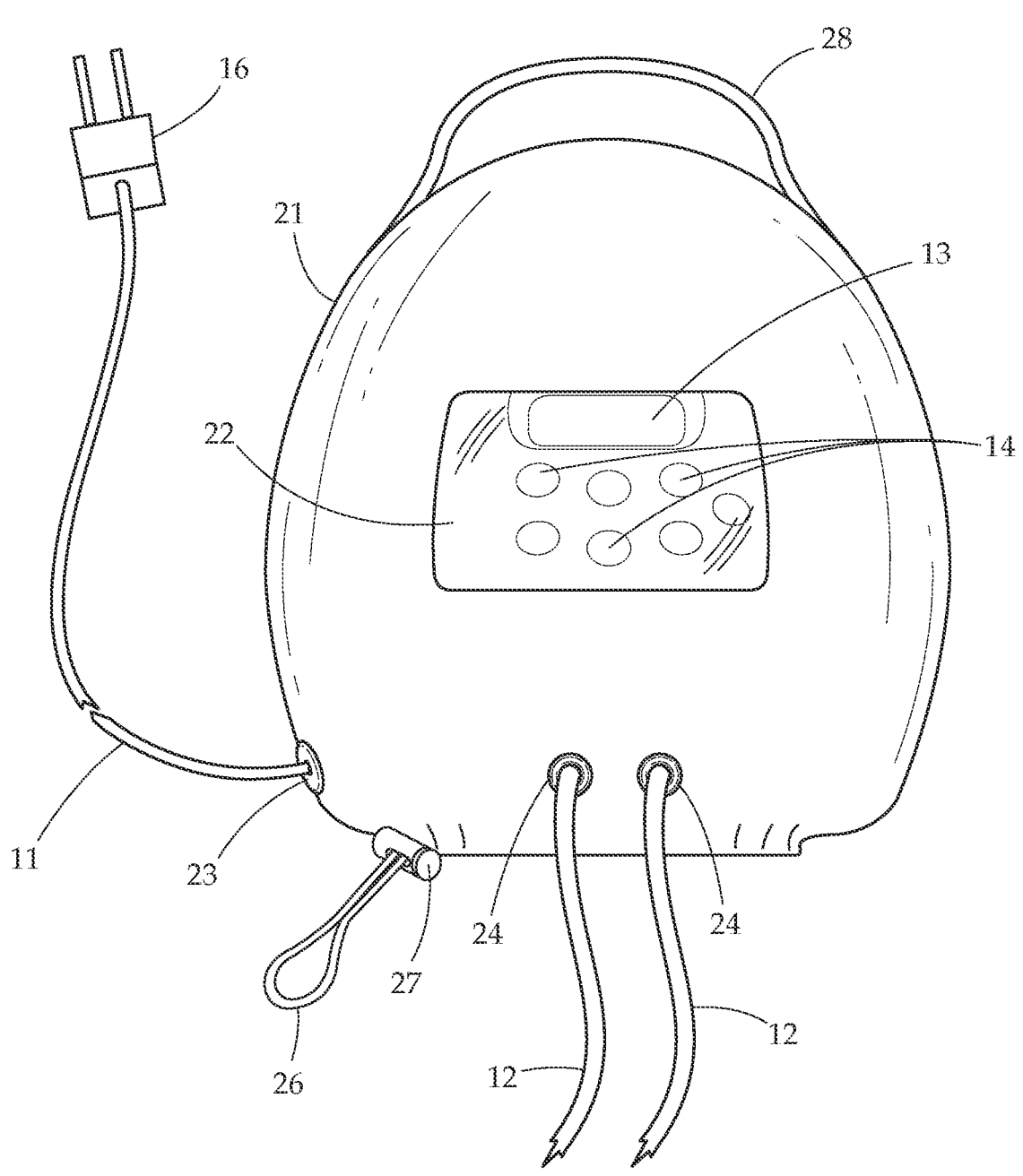
FIG. 4 provides a view of another embodiment of the present disclosure covering the breast pump.

FIG. 3 shows the embodiment of the sound suppressor of FIG. 2, and FIG. 4 shows a view of the sound suppressor of FIG. 2 positioned in place over the breast pump. Notably, the display 13 and buttons 14 are visible and accessible through window 22. Tubes 12 extend from the breast pump through pass throughs 24, while power cord 11 extends through pass through 23 from the breast pump.

Figure 5:
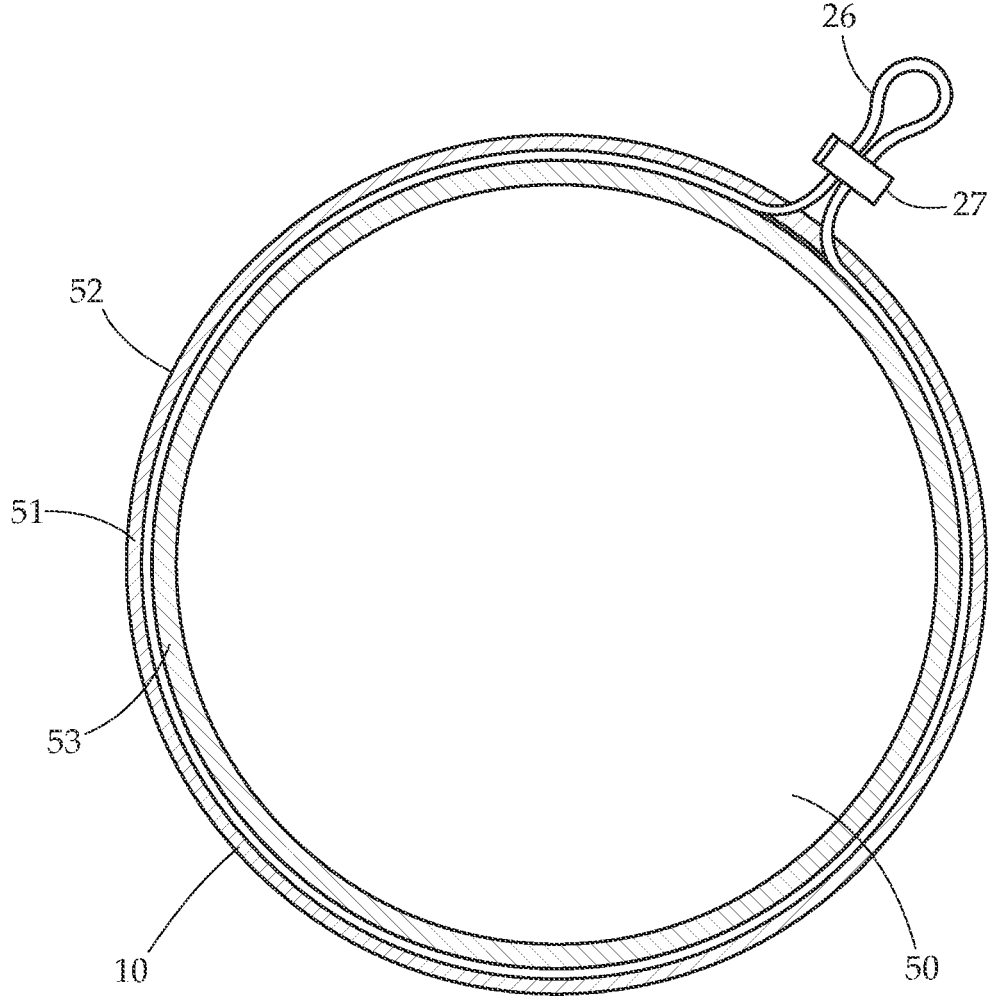
FIG. 5 provides a perspective view of yet another embodiment of the present disclosure.

FIG. 5 provides a view of the sound suppressor showing the opening and interior space of the sound suppressor. The body 21 of the sound suppressor defines opening 50 and an interior space on its inside accessible via the opening 50. Also, a partial cutaway view of this embodiment is shown which shows the sound insulation material 51 contained by an inner layer 53 and outer layer 52. Also visible is the cinch cord 26 extending around a perimeter of opening 50 as well as the cord lock 27.

Figure 6:
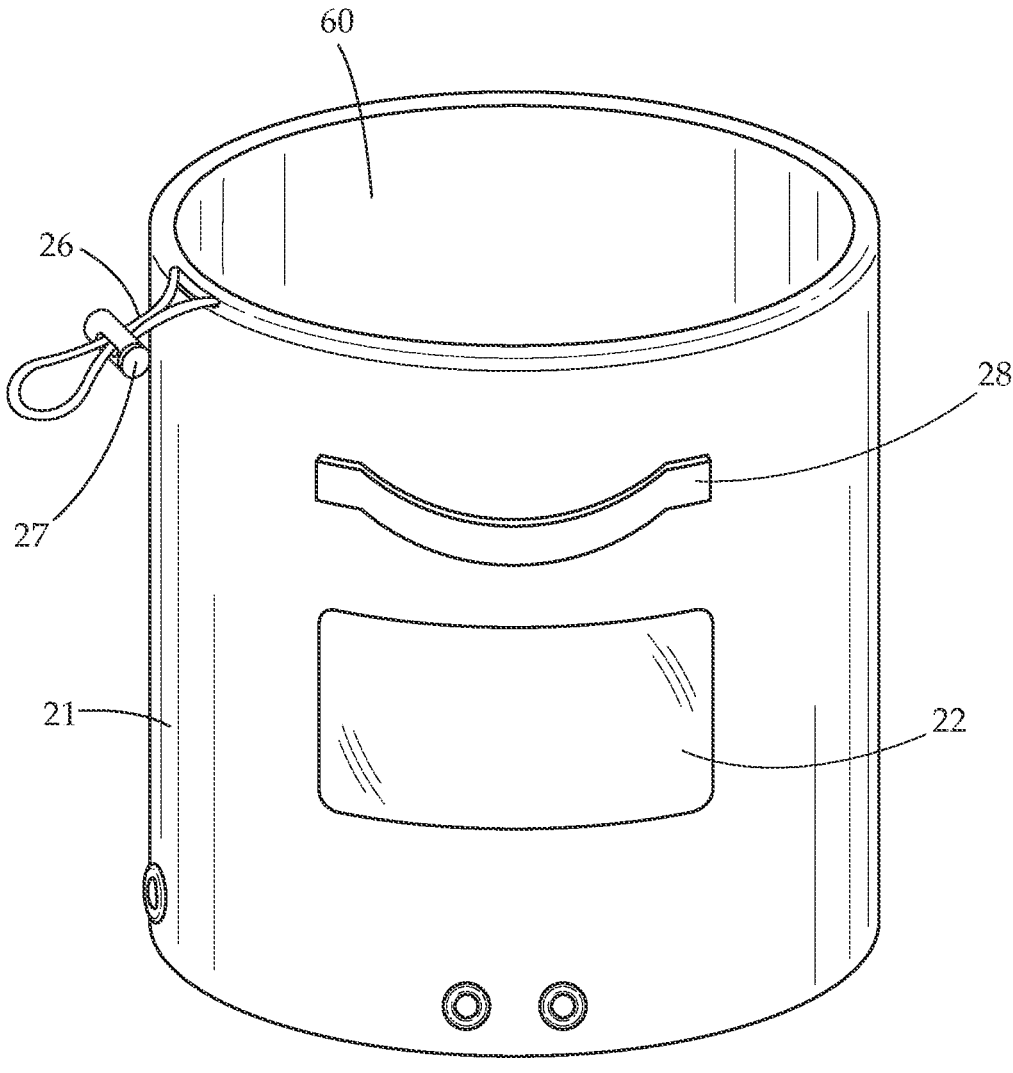
FIG. 6 provides a perspective view of still yet another embodiment of the present disclosure.
Figure 7:
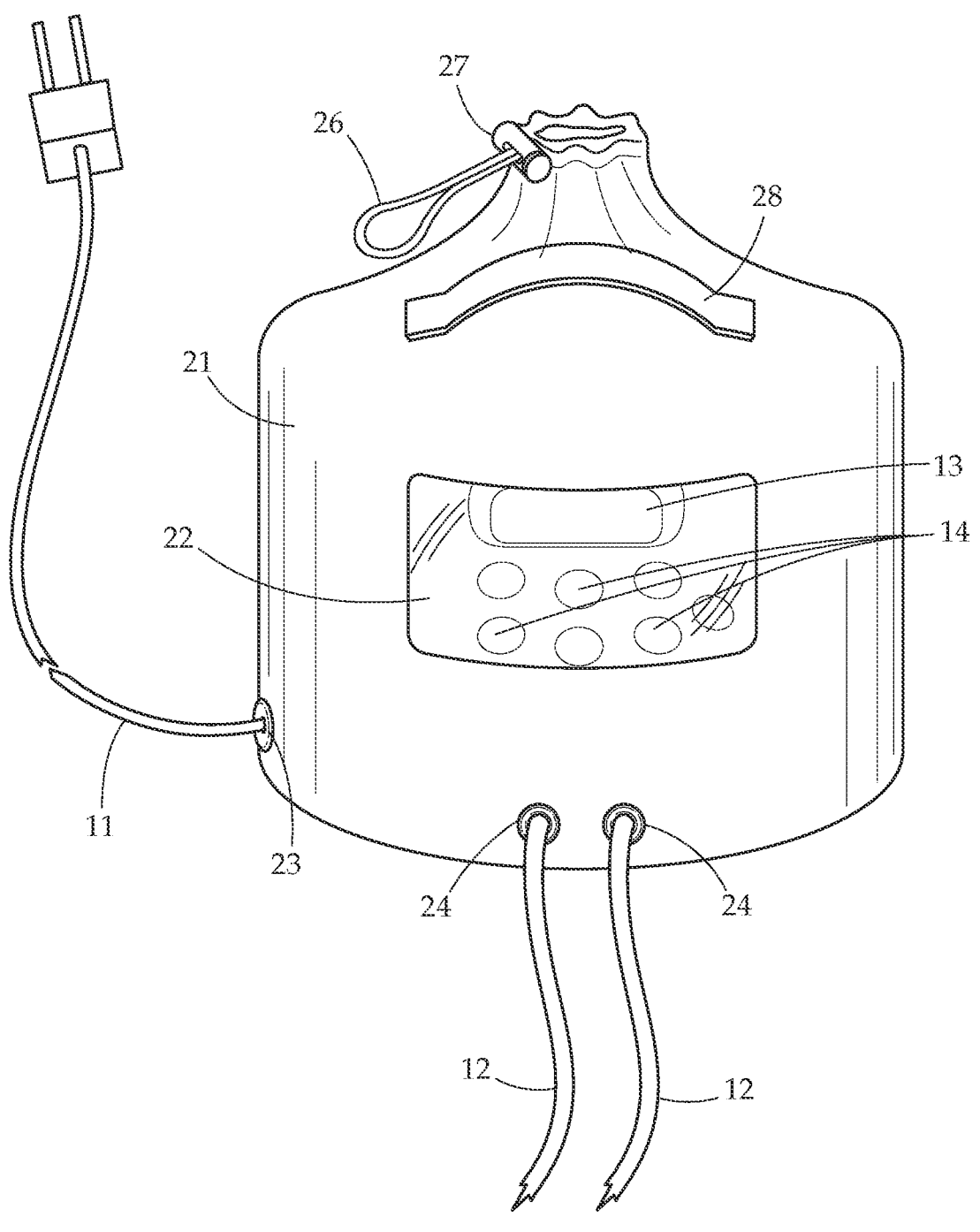
FIG. 7 provides a view of another embodiment of the present disclosure covering the breast pump.

FIGS. 6 and 7 shows views of another embodiment of the sound suppressor having an opening at the top. In such a view, the breast pump is placed into the sound suppressor from the top opening and then the top opening can be closed preventing sound escape. The body 21, formed having a sound insulating material, defines an access window 22 formed, in this embodiment, of a flexible transparent or translucent plastic. This allows viewing of the display 13 and control buttons 14 of the breast pump. Two pass through openings 24 allow passage of the breast pump suction tubes 12. In this embodiment, the pass throughs 24 have a gasket, limiting escape of the sound. Similarly, pass through 23 allows passage of the electrical cord 11. In this embodiment, the pass through 23 has a gasket, limiting escape of the sound. A closure is positioned at the top of the body 21 around the opening 60 at the top. The closure, in this embodiment, is a cinch cord 26 and cord lock 27. The breast pump 10 can be placed into the body 21 from the top through opening 60. Once resting on a bottom of the sound suppressor, the cinch cord 26 is drawn tight and locked in place with the cord lock 27, closing the opening and limiting noise escape. The closed position can be seen in FIG. 7. The cinch cord 26 has been tightened, closing opening 60. Tubes 12 extend through pass throughs 24, and power cord 11 extends through pass through 23. Display 13 and buttons 14 of the pump can be seen and accessed through window 22.

While several variations of the present disclosure have been illustrated by way of example in preferred or particular embodiments, it is apparent that further embodiments could be developed within the spirit and scope of the present disclosure, or the inventive concept thereof. However, it is to be expressly understood that such modifications and adaptations are within the spirit and scope of the present disclosure, and are inclusive, but not limited to the following appended claims as set forth.

What is claimed is:

1. A breast pump sound suppressor, comprising:
    a body formed of a sound-insulating material, defining an interior space, having an opening, and comprising an access window formed of a transparent or translucent material allowing operation of a control system of a breast pump through the access window;
    at least one pass-through extending through the body to allow a passage of one or more tubes or a power cord of the breast pump; and
    a closure operable to substantially close the opening and comprising a cinch cord and a cord lock.

2. The breast pump sound suppressor of claim 1, wherein the body is formed of an outer layer, a sound-insulating layer comprising the sound-insulating material, and an inner layer, wherein the sound-insulating layer is positioned between the outer layer and the inner layer.

3. The breast pump sound suppressor of claim 1, wherein the sound-insulating material is formed of at least one of a foam or a batting.

4. The breast pump sound suppressor of claim 1, wherein the access window is formed of a first layer of transparent plastic spaced from a second layer of transparent plastic.

5. The breast pump sound suppressor of claim 1, wherein the at least one pass-through comprises three pass-throughs, two of the three pass-throughs are sized to receive one of the one or more tubes, and a third of the three pass-throughs is sized to receive the power cord.

6. The breast pump sound suppressor of claim 5, further comprising a gasket disposed proximate each of the three pass-throughs.

7. The breast pump sound suppressor of claim 1, wherein the opening is at a top of the body.

8. The breast pump sound suppressor of claim 1, wherein the opening is at a bottom of the body.

9. The breast pump sound suppressor of claim 1, wherein the opening is at a side of the body.

10. A method of suppressing sound comprising:
    placing a breast pump into the breast pump sound suppressor of claim 1 via the opening;
    connecting the one or more tubes to the breast pump through the body;
    connecting the power cord to the breast pump through the body; and
    activating the breast pump via the control system through the access window.

11. A breast pump sound suppressor, comprising:
    a body formed of a sound-insulating material, defining an interior space, having an opening, and comprising an access window formed of a transparent or translucent material allowing operation of a control system of a breast pump therethrough; and
    at least three pass-throughs extending through the body, wherein two of the three pass-throughs are sized to allow passage of a respective tube connectable to the breast pump and a third of the three pass-throughs is sized to allow passage of a power cord of the breast pump, wherein the body further comprises a gasket in each of the three pass-throughs.

12. The breast pump sound suppressor of claim 11, further comprising a closure operable to substantially close the opening, wherein the closure comprises one or more of a cinch cord or a cord lock.

13. The breast pump sound suppressor of claim 11, wherein the body is formed of an outer layer, a sound-insulating layer comprising the sound-insulating material, and an inner layer and the sound-insulating layer is positioned between the outer layer and the inner layer.

14. The breast pump sound suppressor of claim 11, wherein the opening is at a side of the body, a top of the body, or a bottom of the body.

15. A breast pump sound suppressor, comprising:

a body formed of a sound-insulating material, defining an interior space, having an opening, comprising an access window allowing user operation of a breast pump therethrough, and comprising one or more pass-throughs extending therethrough, wherein at least one of the one or more pass-throughs comprises a gasket; and a closure comprising a cinch cord and a cord lock.

16. The breast pump sound suppressor of claim 15, wherein the one or more pass-throughs comprise first and second pass-throughs that allow passage of a respective tube connectable to the breast pump.

17. The breast pump sound suppressor of claim 16, wherein the at least one or more pass-throughs comprise a third pass-through that allows passage of a power cord of the breast pump.

18. The breast pump sound suppressor of claim 17, wherein the first, second, and third pass-throughs comprise first, second, and third gaskets, respectively.

19. The breast pump sound suppressor of claim 15, wherein at least one of the one or more pass-throughs allows passage of a power cord of the breast pump.

20. The breast pump sound suppressor of claim 15, wherein the one or more pass-throughs comprise a first pass-through that allows passage of a power cord of the breast pump and comprises a first gasket and at least one second pass-through that allows passage of at least one tube connectable to the breast pump and comprises a second gasket.

* * * * *